United States Patent [19]

Terry

[11] Patent Number: 5,242,434
[45] Date of Patent: Sep. 7, 1993

[54] MEDICAL WASTE HANDLING SYSTEM

[76] Inventor: William M. Terry, 135 W. Adams, Ste. 306, Kirkwood, Mo. 63122

[21] Appl. No.: 630,516

[22] Filed: Dec. 20, 1990

[51] Int. Cl.$^5$ ............................................. A61M 1/00
[52] U.S. Cl. .................................. 604/317; 604/322; 604/326
[58] Field of Search ............... 604/317, 318, 322, 326, 604/4, 5, 6

[56] References Cited

U.S. PATENT DOCUMENTS

| | | | |
|---|---|---|---|
| 4,157,718 | 6/1979 | Baehr | 604/317 |
| 4,631,050 | 12/1986 | Reed et al. | 604/317 |
| 4,770,787 | 9/1988 | Heath et al. | 604/4 |
| 4,781,707 | 11/1988 | Boehringer et al. | 604/317 |
| 4,808,159 | 2/1989 | Wilson | 604/4 |
| 4,857,063 | 8/1989 | Glenn | 604/317 |
| 4,867,738 | 9/1989 | Mintz | 604/4 |
| 5,078,677 | 1/1992 | Gentelia | 604/317 |
| 5,154,712 | 10/1992 | Herweck et al. | 604/4 |

Primary Examiner—Randall L. Green
Assistant Examiner—Gina M. Gualtieri
Attorney, Agent, or Firm—Haverstock, Garrett and Roberts

[57] ABSTRACT

An apparatus for collecting, disinfecting and disposing of body waste materials accumulated from a patient including a pair of adjacent collection chambers each having an upper and a lower end, the upper and lower ends respectively being substantially at the same elevations, a first conduit connecting the lower ends of the collection chambers for communication therebetween, a set of conduits connecting the upper ends of the collection chambers, the set of conduits having a smaller cross-sectional flow capacity than the first conduit, an inlet to the first collection chamber at an intermediate location thereon, and an outlet connected to the second collection chamber at an intermediate location thereon, an inlet conduit having a first end for connection to the inlet to the first collection chamber and an opposite open end for exposing to the waste materials to be collected and a conduit for connection to a predetermined environment to establish the environment in the chamber. The present apparatus also includes a unit for connection in the apparatus for collecting, disinfecting and disposing of body waste materials including controls therefor for introducing a rinsing and flushing fluid therein and for supplying a quantity of a disinfectant into the apparatus.

26 Claims, 6 Drawing Sheets

MEDICAL WASTE HANDLING SYSTEM

BRIEF DESCRIPTION OF THE INVENTION

The present invention relates to waste handling systems and particularly to a waste handling system for use in health care facilities such as in operating rooms, patient care rooms, emergency care units and in field care facilities and other places where a person eliminating body waste and needing care may be located. The system includes a collection unit that can use a vacuum or suction source or can be operated using gravity drain to aspirate or otherwise carry away the body waste. The collection unit is preferably portable and is provided with a quantity of a disinfectant that disinfects the waste materials as they are collected. The present invention also includes a servicing unit or module, usually not portable, for servicing and supplying the collection unit with disinfectant. One service unit can service and supply a plurality of the collection units, and the service unit can be located at a convenient place usually some distance from where the waste materials are collected.

BACKGROUND OF THE INVENTION

There are in existance various means for collecting and handling waste materials including body fluids that are aspirated during surgical operation or accumulated for some other reason where a patient is located. Waste materials and body fluids that can be collected using the subject means include blood, urine, mucous and other body discharges. Known waste collection devices and systems include various type of containers into which the collected waste materials are accummulated during surgery and otherwise and from which they are dispensed or poured and sometimes disinfected at a later time. Such devices are usually removed from the place where the collection is made and while the waste materials are still contaminated, and if decontamination is to take place before waste disposal, they are decontaminated or disinfected at some location remote from where they are collected and before discharge into a larger waste recepticle or into a waste disposal system or sewer. The known devices generally do not have any means for effectively separately accummulating waste materials through two or more different suction lines when suction is used, they can not be operated as gravity feed accumulators, they require electrical means and connections for their collection operations, they require the handling and disposing of the accummulated waste materials often before the waste materials are disinfected and therefore present a danger to the handlers, they can be spilled while still contaminated, and most known systems require filters and other devices which must be removed and replaced from time to time and which may adversely effect their operation. The moving about and otherwise handling and transporting the waste materials before they are decontaminated presents an unacceptable risk of infection to all personnel that are responsible for handling and disposing of their contents. Typical of known devices are the devices disclosed in Parker U.S. Pat. Nos. 4,863,446 and 4,957,491.

SUMMARY OF THE INVENTION

The present invention teaches the construction and operation of means which overcome the disadvantages and shortcomings of the prior art and contains important improvements not available in waste handling devices heretofore. To this end the present invention teaches the construction and operation of a waste collection and handling system which has one unit which is used to collect and disinfect waste materials immediately on collection and a second service unit for servicing and resupplying the collection system. Each collection unit is serviced and supplied with a quantity of disinfectant before each use and can be used during surgical procedures as well as in almost any other patient care location and situation where the patient produces waste materials. The collection and disinfecting unit, when being used in an operating room or other environment can be operated off of existing suction lines for the rapid accummulation of waste materials including body fluids and the like or it can be operated as a gravity feed or gravity drain collection device. The collection unit contains a supply of a disinfectant such as sodium hypochloride that disinfects the waste materials as soon as they enter the collection chamber and are exposed to the disinfectant. This greatly reduces or completely eliminates the possibility that personnel handling the collected materials will come in contact with infected waste materials and be infected thereby. This is true even in the unlikely situation where the collection unit might be upset or overturned or otherwise should spill its contents. The collection unit is also preferably provided with an anti spill feature.

The servicing unit, usually is located remote from the collection unit, which servicing unit is relatively easily connected to the collection unit for rinsing, cleaning, flushing and decontaminating it, and for supplying it with a fresh supply or charge of a disinfectant material which will enable it during its next use to disinfect waste materials as they are collected.

The collection unit can also be constructed to have replicative means for accummulating waste materials using one or more suction lines so that waste materials can be collected simultaneously from several different locations, and the separate suction collection means, when used, will not adversely effect one anothers operation. Separate collection means may not be required when gravity drain collection is taking place. The present collection unit can also be made in many sizes and shapes to accommodate different environments and procedures.

OBJECTS OF THE INVENTION

It is a principal object of the present invention to make the accummulation, handling and disposal of waste materials safe.

Another object is to enable body fluids to be collected simultaneously and effectively from one or more different locations using vacuum or gravity collection procedures.

Another object is to disinfect body waste materials immediately as they are collected and accummulated.

Another object is to collect, disinfect, and dispose of waste materials in a safe, efficient manner and without the possibility for any person handling or operating the collection means coming in contact with contaminated waste materials.

Another object is to provide a relatively compact easy to use means for collecting and decontaminating waste materials and particularly waste materials collected from patients in a hospital, a nursing home or elsewhere.

Another object is to reduce the possibility of infection to personnel responsible for handling and disposing of waste materials collected during surgical and other patient procedures.

Another object is to teach the construction and operation of a portable unit for use in collecting waste materials including body fluids which requires no electrical support means during the collection and decontamination of the body fluids.

Another object is to teach the construction of a collection device having separate fluid collection chambers and means for equalizing the pressure therebetween.

Another object is to teach the construction of a collection device capable of being operated off a vacuum source without requiring any baffles or other barriers to prevent the collected fluids from entering and blocking the connection to the vacuum source.

Another object is to teach the construction of relatively simple means for establishing a desired depth of a disinfectant material used in a collection chamber.

Another object is to provide means for predeterminately adjusting the strength of vacuum used to aspirate waste materials into a collection container.

Another object is to provide relatively simple and efficient means for rinsing, cleaning, flushing and recharging a unit used for collecting body waste and like materials.

Another object is to provide means in a waste collection device for separating the cleaning and other fluids that may be present from a vacuum source that is used.

Another object is to provide connection means on a unit used for collecting waste materials such as body fluids, which connection means can be used for several purposes including for connection to a source of vacuum, for connection to a source of rinsing and flushing fluid, or can be left open to atmosphere when the unit is used as a gravity drain collection device.

Another object is to teach the construction and operation of means used for collecting and decontaminating body fluids, which unit can be rinsed, flushed and supplied with a disinfectant material in minimal time, with minimal rinsing and flushing fluid and with minimal operator attention.

Another object is to provide a waste collection system that includes a waste collection unit and a service unit therefor both of which are constructed to minimize or eliminate areas or places where infected materials can accumulate or be trapped.

Another object is to provide means on a device for collecting body waste materials and the like which includes means for continuously and smoothly indicating the amount of materials collected.

Another object is to provide a two chambers container into which body fluids and the like are collected, which container has one portion into which the collected fluids are deposited and another portion in communication therewith.

Another object is to provide means used in the collection of waste fluids which feed the incoming materials through a relatively large diameter conduit in a straight horizontal plane in a manner that prevents clogging or barriers.

These and other objects and advantages of the present invention will become apparent after considering the following detailed specification disclosing a preferred embodiment of the invention in connection with the accompanying drawings.

DESCRIPTION OF A PREFERRED EMBODIMENT

Figure 1:
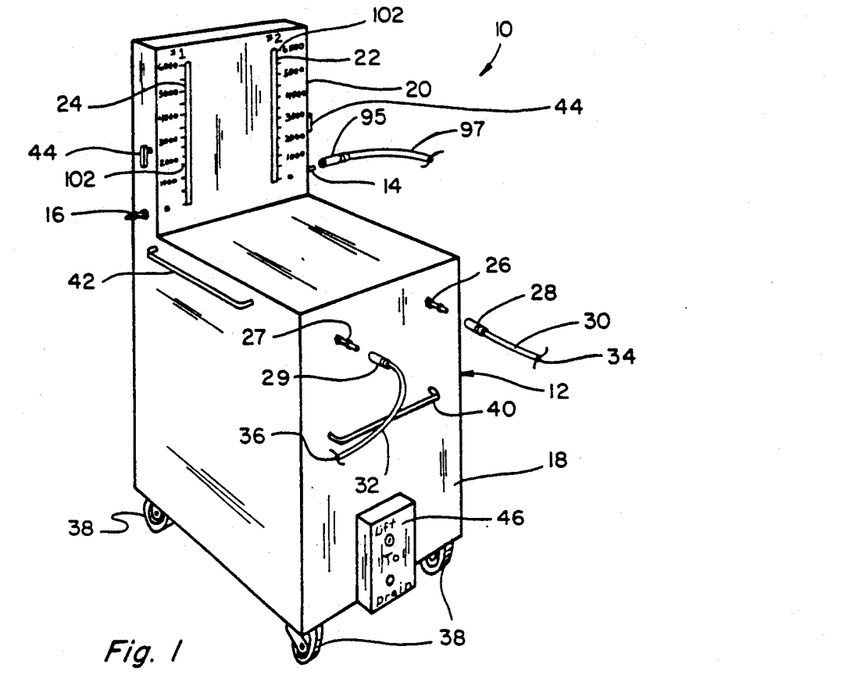
FIG. 1 is a perspective view of a unit for use in collecting, disinfecting, handling, and disposing of waste materials and particular fluid waste materials such as body waste material; said unit being constructed according to the teachings of the present invention.

Referring to the drawings more particularly by reference numbers, number 10 refers to a waste collection unit for use in receiving, disinfecting, storing and disposing of waste materials such as body fluids. The unit 10 is shown having a housing 12 for accommodating two sets of collection means or containers each of which is shown having a suction connector means or fitting 14 and 16. The same connections can also be used when the device is used as a gravity feed collection device. If gravity feed is used, it may be possible to use fewer container pairs or pairs of waste collection compartments or chambers. The unit 10 can also be made in models for use in the emergency rooms and for use in intensive care units, which models may only have one set of treatment chamber or containers. The housing 12 has a lower portion 18 inside of which are located the collection means including the collecting container pairs and the fittings, conduits and connections therefor, and it has an upstanding housing portion 20 in which are mounted gage means 22 and 24 for indicating the amount of waste fluids that have been accumulated in the several sets or pairs of collection chambers or containers. The housing portion 18 (or 20) also has fittings 26 and 27 which are used when either suction or gravity drain is to be used. These fittings are coupled to fittings 28 and 29 on the ends of associated conduits 30 and 32, the opposite ends 34 and 36 of which are positioned near to where the waste materials are to be aspirated or drained for accumulation. If the inlet end 34 of the conduit 30 is positioned near to a location where body fluids are accummulating the fluids will enter or be aspirated through the conduit 30, through the coupled fittings 26 and 28 and into collection means located inside of the lower container portion 18. The conduits 30 and 32 are usually made of a disposable material so that once used and contaminated they can be thrown away or otherwise disposed of.

The conduits 30 and 32 may have ends 28 and 29 which snap or slide onto and couple to the suction fittings 26 and 27. Also, if the unit 10 is used in an operating room equipped with one or more suction connections or fittings these can be connected by flexible tubes or the like to the inlet fittings 14 and 16 on the unit 10. Except for possibly having suction connections to the inlet fittings 14 and 16, the collection unit 10 does not require any other connections such as electrical power connections and the like when it is being used to collect waste.

The collection unit 10 is shown mounted on casters or wheel assemblies 38 which make it portable and enable it to be easily moved about including into a patient room, an operating room or to and from a location including to and from a location where it is to be serviced and resupplied or recharged with disinfectant. To facilitate its movement the unit 10 is also provided with suitable handles such as handles 40 and 42 which are shown attached to its front and sides. The device also has control levers 44, one of which is associated with each inlet fitting 14 and 16 and is movable between two extremes labeled ON and OFF. The setting of the lever 44 for each inlet controls the amount of opening provided to the suction source or to atmosphere in the case of gravity feed and hence the strength of the suction or drain that is used. The lever 44 will have only "on" or "off" positions when used with a gravity feed system.

Mounted on the front wall of the lower housing portion 12 is a movable cover panel 46 which has on it the legend "Lift To Drain". The panel 46 can be raised to expose a drain fitting and an electrical receptacle, both of which can be connected to means on the service unit which will be described later. A sensing mechanism or interlock may also be provided which will not allow operation of the servicing unit until both the drain and the electrical connector have been properly connected.

Figure 2:
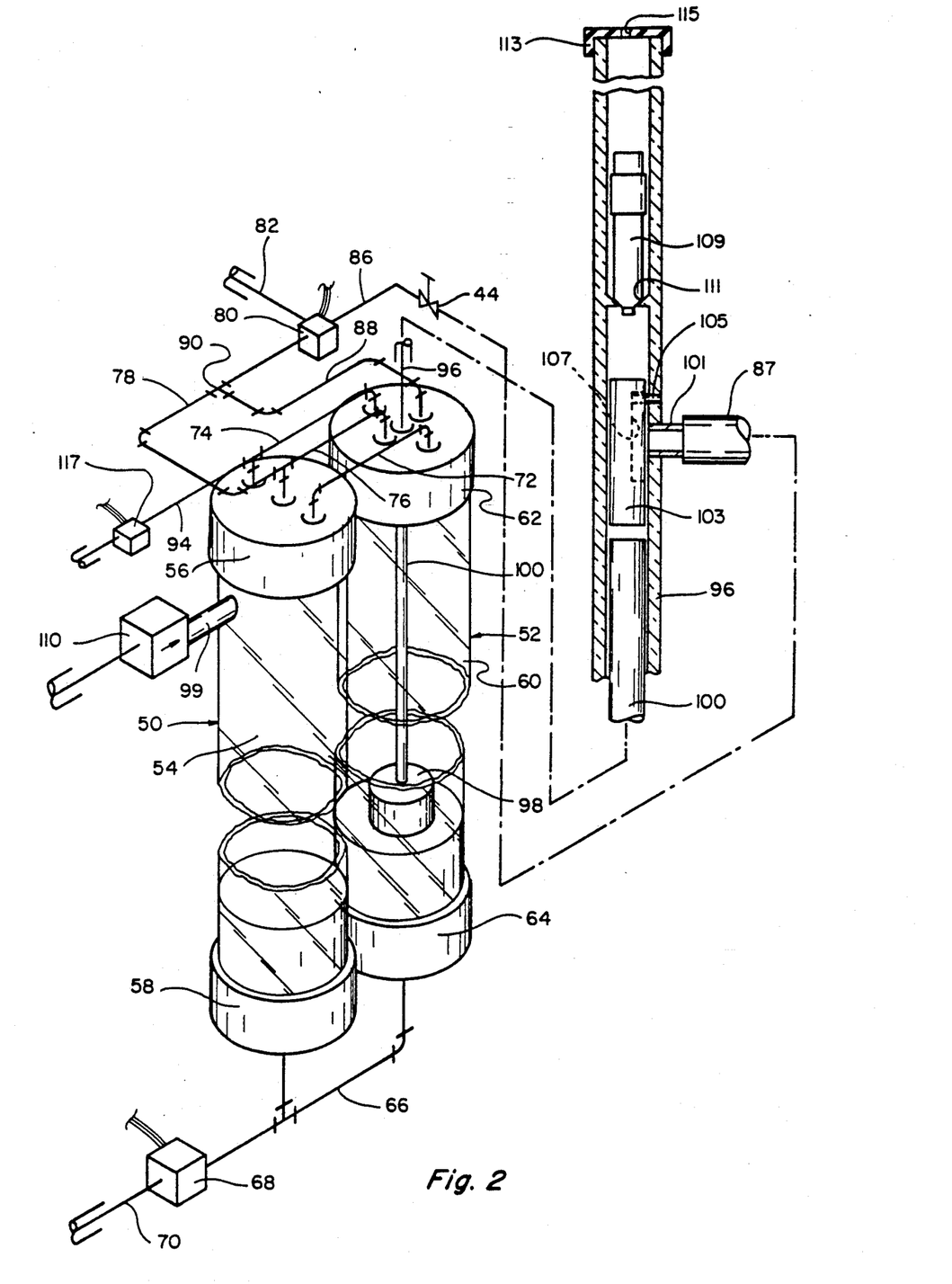
FIG. 2 is a perspective view of one collection portion of the means of FIG. 1 showing the connections therefor.
Figure 7:
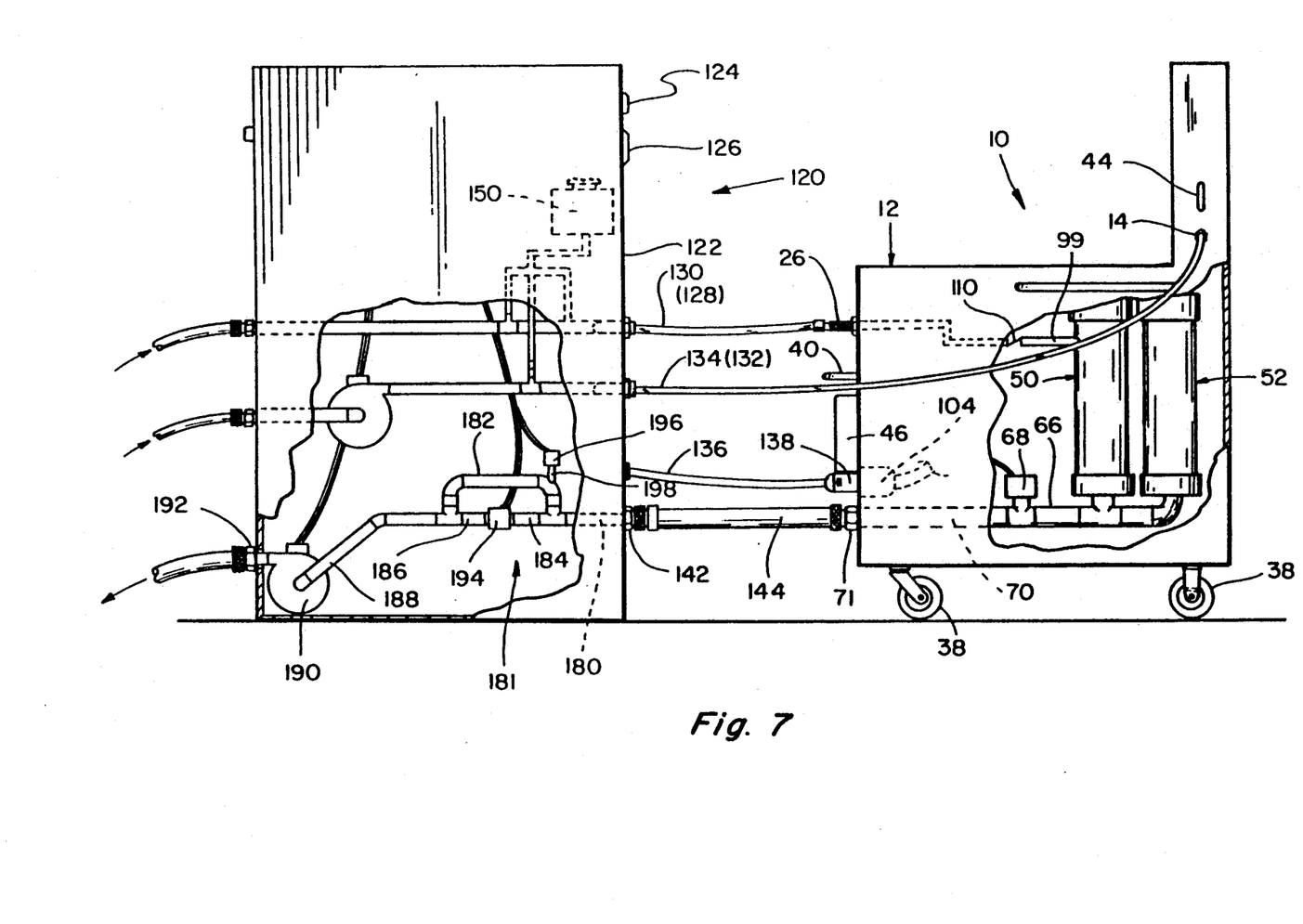
FIG. 7 is a side elevational view showing the collection unit of FIG. 1 connected to the servicing unit of FIG. 5 for rinsing, cleaning, flushing and supplying disinfectant thereto.

FIG. 2 shows a pair of closed tubular containers 50 and 52 which are operated as a pair and are able to service one suction inlet conduit such as the suction conduits 30 or 32 or any desired number of gravity feed inlets conduits. The containers 50 and 52 are connected by various conduits or tubes to operate in a particular manner and the construction and operation of the containers is important to the present invention. The container 50 includes a vertically oriented tubular portion 54 which is substantially closed at its upper and lower ends as by closure members 56 and 58. In like manner the container 52 has a vertically oriented tubular portion 60 closed at its upper end by closure member 62 and at its lower end by closure member 64. The lower end closures 58 and 64 are connected and communicate through a conduit 66 which provides relatively unlimited communication therebetween. The conduit 66 is also connected to one side of a normally closed solenoid operated drain valve 68, the opposite side of which is connected to discharge conduit 70 which extends to drain fitting 71 located on the front wall of the housing 12 (FIG. 7). An electric actuator with a two way ball valve can also be used instead of the valve 68.

The upper container closure members 56 and 62 are connected by other conduits all of which together are of more restricted flow capacity than the conduit 66. These conduits include vacuum equalizing conduits 72 and 74. The purpose for the conduits 72 and 74 is to minimize or eliminate any vacuum differential that otherwise might exist between the insides of the containers 50 and 52 and yet enables the containers to receive body fluids and other waste materials when the system is operating and particularly when operating on suction. This pressure equalizing affect also maintains the liquid level in the containers 50 and 52 substantially the same at all times. If too large or too small a conduit size is used to connect the upper ends of the containers the system will not operate at its best. This will be explained more in detailed hereinafter.

The upper ends of the containers 50 and 52 also communicate through another conduit 76 which is connected to conduit 78 and is blocked by a electrically actuated three way ball valve 80 when the unit 10 is being used to collect waste materials. The valve 80 is energized and open when the system is being rinsed, flushed and cleaned and is receiving a water with a fresh supply of disinfectant as will be explained. The valve 80 has an inlet that is connected to the vacuum or gravity drain inlet 14 or 16 through conduit 82 when collecting waste and to a source of drain water and disinfectant when being flushed and cleaned.

The opposite side of the valve 80 is connected by tube 86, the manual control valve 44 and by tube 87 and fitting 101 to the inside of tube 96 which will be described in connection with FIG. 2, which connection applies vacuum to the inside containers 50 and 52. Another conduit 88 is connected to the upper end of the closure member 62 of the container 52 and to the conduit 78 by means Of T-connector 90.

Referring again to FIG. 2 there is shown on the right the upper end portion of the tube 96 (shown enlarged and in cross section), and the upper end portion of rod 100 that extends therein and which will be described later. The lower end of the rod 100 is connected to float 98 so that as the liquid in the containers 50 and 52 rises the upper end of the rod 100 will move upwardly eventually moving against a member 103 located in the tube 96. As the rod 100 continues to move upwardly, being guided in its movement by cooperation between pin 105 and groove 107 formed in one side of the member 103, the member 103 will move upwardly against the lower end of moveable valve member 109 which is engaged with valve seat 111. As soon as the valve member 109 moves out of engagement with the valve seat 111, it will establish communication through the tube 96 directly into the chambers 50 and 52. This communication will destroy the vacuum present in the chambers 50 and 52 and will prevent further body fluids from being aspirated into the container 50, and the collection process will stop. This feature provides overflow protection. If the device is operating on gravity drain instead of vacuum the operation will continue as before. The upper end of the tube 96 may be partially closed by a cap 113 with an orifice 115 therein.

The containers 50 and 52 have an inlet ports connected by conduits 74 and 94 to a solenoid valve 117. The valve 117 is normally closed and electrically opens during connection to the servicing unit to allow air to enter the otherwise closed upper ends of the containers to facilitate passage of the flushing and rinsing fluid into the system. The fitting 14 (or 16) cooperatively connects as by connector 95 to one end of a suction line 97 when suction is used, otherwise if gravity feed is used, no connection to the fitting 14 (or 16) is required. The same fittings 14 and 16 are connected to the source of flushing and rinsing fluid when the unit 10 is connected to the service unit.

The container 50 also has an inlet connection through conduit 99 to the waste inlet fitting 26 (or 27) so that waste materials can be aspirated or drained into the container 50 through the conduit 30 (or 32). It is important to recognize that as the waste materials enter and are collected in the container 50, any splashing or tubulence that occurs will take place in the container 50, and not in the container 52 which has the suction connection or the connection to atmosphere. This means that no tubulance or splashing will take place in container 52 due to the collection of waste and hence there is no chance for waste material to enter and clog the suction or atmosphere inlet.

The container 52, which is the rear container, has vertical transparent tube 96 connected to the upper closure wall 62, and the container 52 contains the float 98 which is shown connected to the upwardly extending rod member 100 which extends upwardly into the tube 96. The tube 96 may have a graduated scale 102 imprinted or otherwise formed thereon or located on the adjacent housing portion 20. The position of the upper end of the rod 100 on the scale 102 indicates the total amount of waste materials or fluid that has accummulated in the containers 50 and 52. The fact that the float 98 is in the rear containers 52 instead of in the front container 50 means that it also is not effected by any of the turbulence created by the incoming fluids, and this means that there will be a steady smooth movement of the float 98 and of the rod 100 connected thereto.

Figure 3:
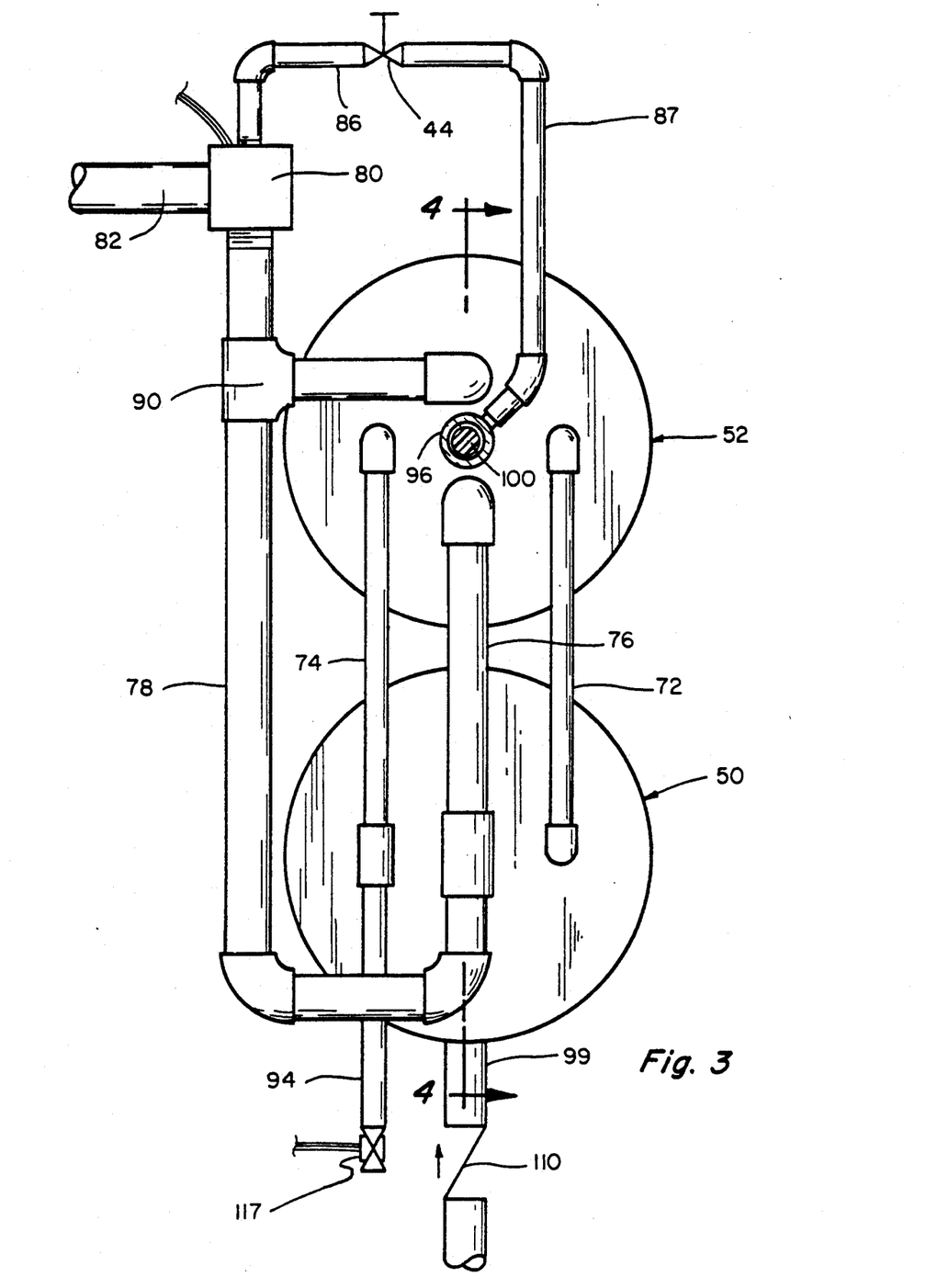
FIG. 3 is a top plan view of the collection portion shown in FIG. 2.
Figure 4:
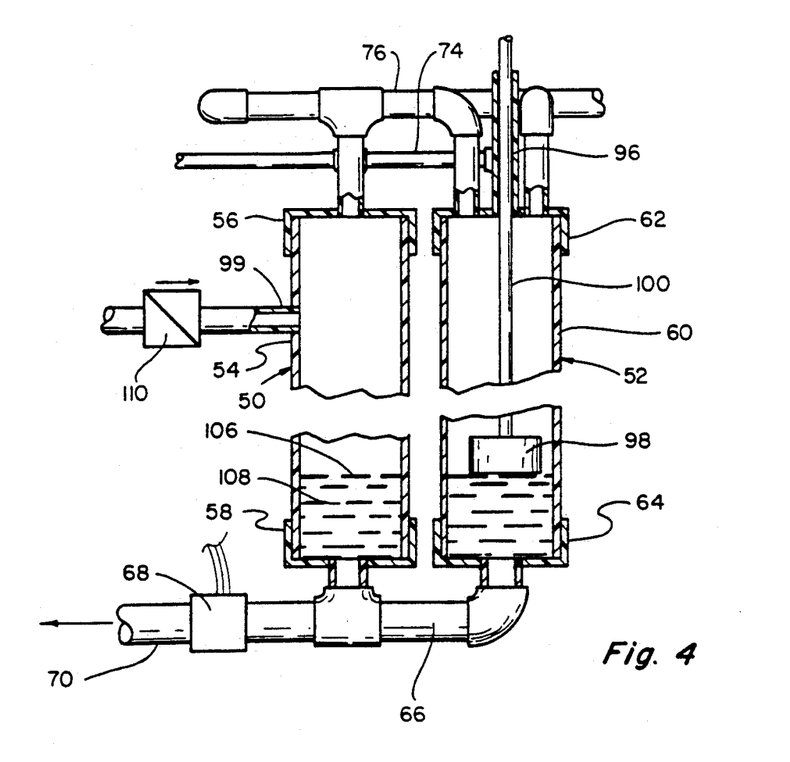
FIG. 4 is a cross sectional view taken on line 4—4 of FIG. 3.

FIGS. 3 and 4 show many of the same connections described above including also showing electrical connections to the solenoids 68 and 117, all of which are connected to and through an electric receptacle 104 located o the front of the housing 12. The receptacle 104 is only used when the unit 10 is connected to the service unit as will be explained.

FIG. 4 is a cross sectional view showing more of the details of the construction of the containers 50 and 52 including also showing the containers filled to a predetermined level 106 with a liquid disinfectant 108. Each time the unit 10 is serviced a supply of the disinfectant 108 is placed in the containers 50 and 52 from the service unit so that the unit 10 is again ready to collect waste materials. This means that disinfectant is present in the containers 50 and 52 at all times including when the body fluids are being collected from a patient and until they are flushed out and replaced. The disinfectant is normally supplied with the flushing water making the servicing that much simpler.

Depending on how fast the body fluids being collected enter the container 50 will determine to some extent how they enter and fall into the disinfectant. Regardless of how they enter, however, they will fall into the disinfectant which will kill bacteria or other infectious materials that may be present making the fluids, as collected, safe to handle and/or come in contact with. This is very important to the present invention because it means that simultaneously with the collection of the waste fluids from the patient they are disinfected and become harmless and safe to come in contact with. This also means that even if the unit 10 should overturn or otherwise be damaged or the contents spilled the contents will be decontaminated and will not be a danger to anyone. The device is also provided with a check valve 110 located in the inlet conduit 99 (FIG. 2) that serves as an anti spill feature for the inlet conduit 99.

Figure 5:
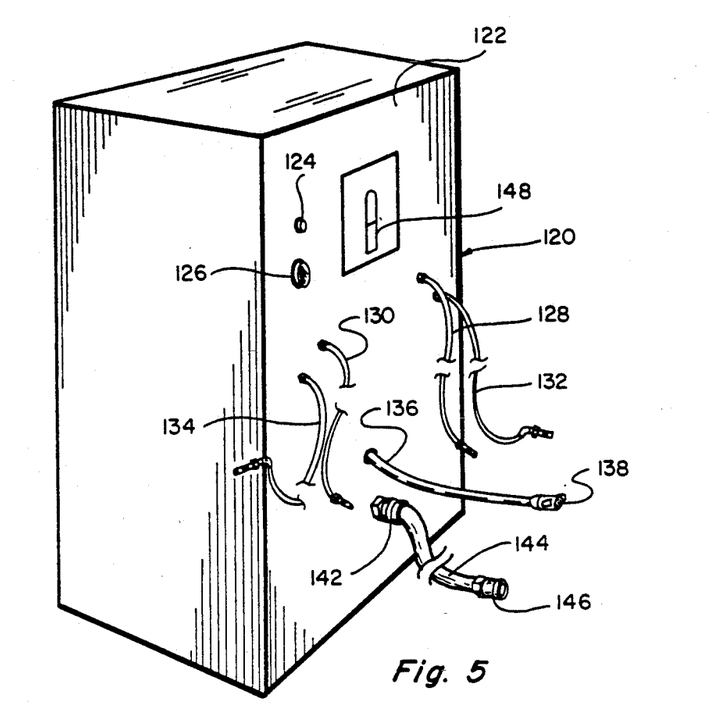
FIG. 5 is a perspective view of a servicing unit for rinsing, cleaning, flushing and supplying disinfectant to the unit shown in FIGS. 1-4.

FIG. 5 is a perspective view of the service unit 120 used for rinsing, flushing, cleaning and supplying the disinfectant 108 to the containers 50 and 52. The service unit 120 which can be located at any convenient location has means for making both fluid and electrical connections to the unit 10. The unit 120 also has a connection to a source of electric energy, to a source of rinsing fluid such as to a source of hot and cold water, and to a drain line such as to a sewer system. The assembly 120 flushes hot and cold water or a mixture thereof through various conduits and into the containers 50 and 5 in the unit 10 to flush out the containers and the conduits associated therewith and to dispose of the waste materials contained therein. The unit 120 also supplies the containers 50 and 52 with a fresh supply of disinfectant which is supplied up to a predetermined level. Since the unit 120 is normally maintained in a fixed position, and the collection units 10, which are portable, brought to it for connection, the relative elevations of certain parts of the units 10 and 120 when connected is important in order for the service unit 120 to be able to supply disinfectant to the predetermined level. This is done automatically at the conclusion of the rinse and flush cycles. Servicing is preferably fully automatic and requires only a short time to complete. Timer control means or a microprocessor are used to control the rinsing, flushing and supplying of disinfectant.

The service unit 120 has a front panel 122 where a plurality of connection means are made including a connection to a source of electrical energy, an electrical connection to the unit 10, a connection to a source of rinsing and flushing fluid such as hot and cold water and an outlet drain connection. The front panel 122 of the service unit 120 also includes a system "ON" light 124 which indicates when the system is turned on, a start button 126 which is pressed to cause the system to operate when properly connected to the unit 10, and conduits 128, 130, 132 and 134 which are flexible conduits connected to respective ones of patient inlets or fittings 26 and 27 and 14 and 16 on the unit 10. The front panel 122 also has a power cable 136 extending therefrom with a male receptacle 138 for cooperating engagement with the female receptacle 104 on the unit 10. Near the bottom of the unit 120 is another fitting 142 which is connected by conduit 144 and fitting 146 to the drain receptacle 71 on the portable unit 10. Near the top center of the panel 122 is a visual indicator 148 behind which is located a transparent container 150 of disinfectant (FIG. 6).

Figure 6:
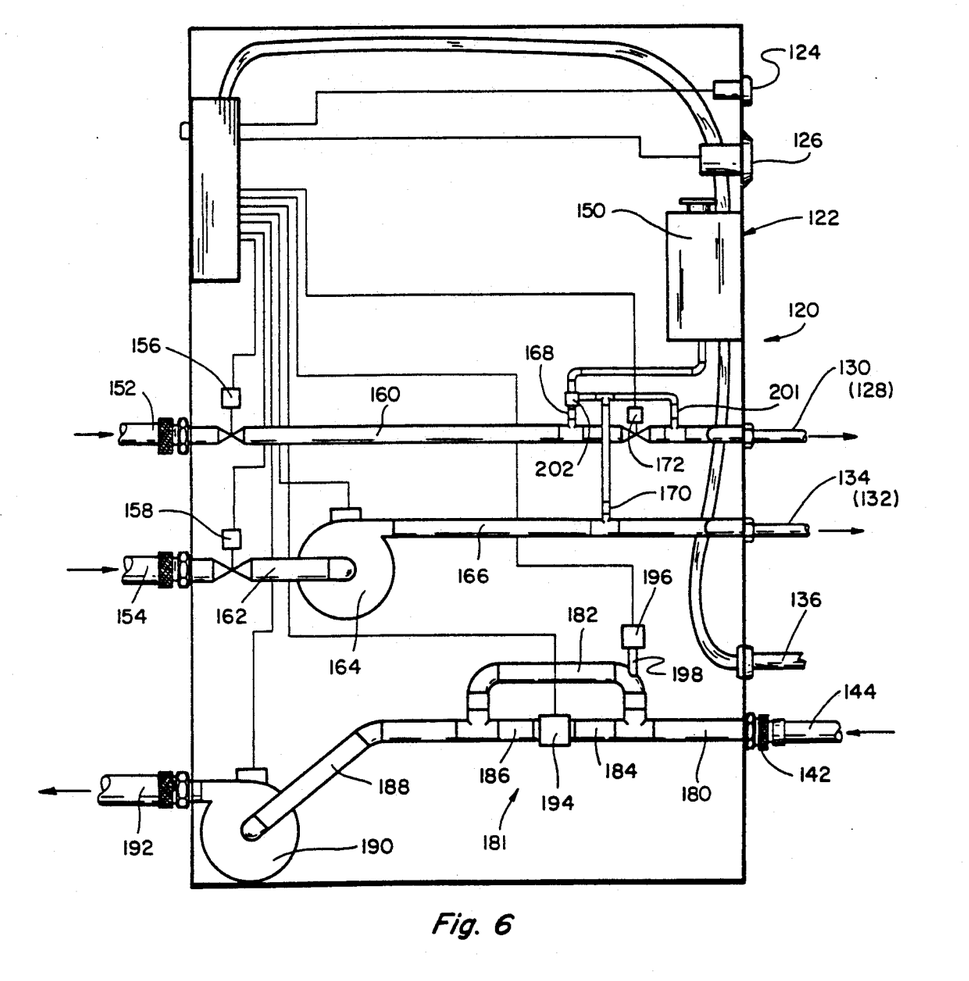
FIG. 6 is a schematic diagram showing the components and connections of the servicing unit shown in FIG. 5.

FIG. 6 shows more of the details of the construction of the fluid and other connections in the servicing unit 120 and should be considered together with FIG. 3 and 4 to better understand how the connections are made between the servicing unit 120 and the collection unit 10.

The servicing unit 120 includes hot and cold water inlet conduits 152 and 154 which are controlled by respective solenoid valves 156 and 158 shown schematically. The outlet side of the hot water valve 156 is connected to conduit 160 and the outlet side of the cold water valve 158 is connected by conduit 162 to water pump 164. The hot water conduit 160 is a straight through flow conduit that has its outlet end connected to directly supply hot water to the unit 10 through flexible conduits 128 and 130 (FIGS. 6 and 7). The outlet side of the cold water pump 164 is connected through conduit 166 to feed cold water through flexible conduits 132 and 134 to and through the fitting 14 and 16 and through the conduit 82 into the containers 50 and 52. Both of the conduits 160 and 166 also have disinfectant inlet connections which are connected through conduits 168 and 170, respectively, which in turn supply predetermined amounts of disinfectant thereto through an adjustable injector 202 from the disinfectant container 150 located in the position shown. Whenever the servicing unit 120 is operating and flushing liquid through the unit 10, the solenoid valve 172 will be energized to redirect some flushing liquid through conduit 168, and injector 202 to permit some disinfectant to flow from the source container 150 through the conduits 201 and 170 into the water conduits 160 and 166. An appropriate amount of disinfectant will be permitted to enter each of the water conduits, and this amount is determined by the concentration required to disinfect the waste. A suitable disinfectant for this purpose, as indicated above, is sodium hypochloride although other disinfectants can also be used as required.

As explained above, when the patient unit 10 is operating to aspirate or drain body fluid waste into the containers 50 and 52 there is no need for any electrical connections to the unit 10. This is important because it eliminates the need for electrical connections at the point of use such as in a patient care room or in an operating room and it adds to the safety and convenience of the device making it usable almost anywhere. It also means that the various valves used in the unit 10 will have either normally open or normally closed conditions and will remain in those conditions until the unit 10 is connected to the flushing and draining unit 120. When this takes place electrical connection 136 between the units 10 and 120 is established so that when the unit 10 is to be flushed and cleaned by pressing on the start switch 126, the device will go through an automatic cycling process under control of a timer mechanism or a microprocessor. Pressing the switch 126 will cause the solenoid valves 68, 80 and 117 in the unit 10 to be energized and to change from their normal positions to their energized or transferred positions which are the positions necessary to enable circulation of the decontaminated flushing and rinsing water through the system for cleaning, rinsing and flushing the unit 10, and thereafter for establishing the desired amount of decontaminant that will remain in the containers 50 and 52. By introducing the decontaminant into the flushing water it enables the unit to be rinsed and flushed with minimum water and in minimum time and at the conclusion thereof to establish the desired level of decontaminant which is already in the rinse water.

In FIG. 6 it was shown that the reservoir 150 for the decontaminate has the connections 168 and 170 to the hot and cold water conduits 160 and 166 and these conduits are connected to the unit 10 at the upper ends thereof through conduits including conduit 82 and through normally closed solenoid valve 80 which is now open, and through the conduits 78 and 88 where their outputs are fed into the upper ends of the containers 50 and 52 through spray nozzles or the like as well as through the conduit 99. Most of the incoming water used for flushing and rinsing will enter the containers 50 and 52 through spray nozzles located inside of the containers so that there will be a thorough washing and flushing of each of the containers. As the rinse water feeds into and accumulates in the containers 50 and 52 it will drain out the bottom through the conduit 66 and through the normally closed drain valve 68 into conduit 70. From there the rinse water will flow through the conduit 144 (FIG. 7) into conduit 180 which is part of the drainage system of the unit 120.

The drainage system includes an inverted trap assembly 181 made up of connected conduits 182, 184 and 186 connected as shown. The output side of the trap assembly 181 is fed through a conduit 188 to and through drain pump 190 which has its outlet 192 connected to a waste disposal system or sewage line (not shown). The trap assembly 181 also includes a normally open solenoid valve 194 which is positioned between the communicating conduits 184 and 186. The drain valve 194 is a normally open valve which closes during a flushing operation to cause the flushing water to flow through the conduit 182 at the conclusion of the rinsing cycle so that there will be flushing water with disinfectant standing in the conduits 182 and 180. This water will continue in this condition after the rinse cycle is completed and will establish the same level for the liquid in the containers 50 and 52. This can be seen in FIG. 7 which shows the upper reach of the conduit 182 at a desired level for the decontaminate in relation to the containers 50 and 52.

Once the rinsing and decontamination cycles have been completed, the solenoid valve 68 (FIGS. 6 and 7) will be deenergized and return t its normally closed condition. The water remaining in the conduits 70, 144, 180, 182, 186 and 188 will then be cut off from the water in the containers 50 and 52 and the subsequent energizing of the valve 194 will enable the remaining liquid in these conduits to drain out to the sewer line. The opening of the valve 194 will enable the material contained in the trap assembly including the associated conduits back to the valve 68 to completely drain through the pump 190 and this is desirable since it is preferred not to have any excess water or drainage fluid in the system. This is made possible by the opening of another valve 196 which when open operates through conduit 198 connected to the trap conduit 182 to expose the trap assembly to atmospheric conditions. Once this is done the units 10 and 120 can be separated from each other, and the unit 10 is now ready to be used in another patient drainage or suction procedure. By the same token the assembly 120 can now be connected up to another unit 10 for cleaning, draining and supplying a fresh supply of decontaminant thereto. It is contemplated to have the operator (or the factory during manufacture) adjust the duration of the wash, rinse, drain and refill cycles as desired.

It is preferred to make all of the conduit and fitting connections have smooth inner surface as by tapering the connectors. This is done to minimize or eliminate places where waste or rinse water can be trapped. The parts should also be made of materials that are not affected by bacteria action.

Figure 8:
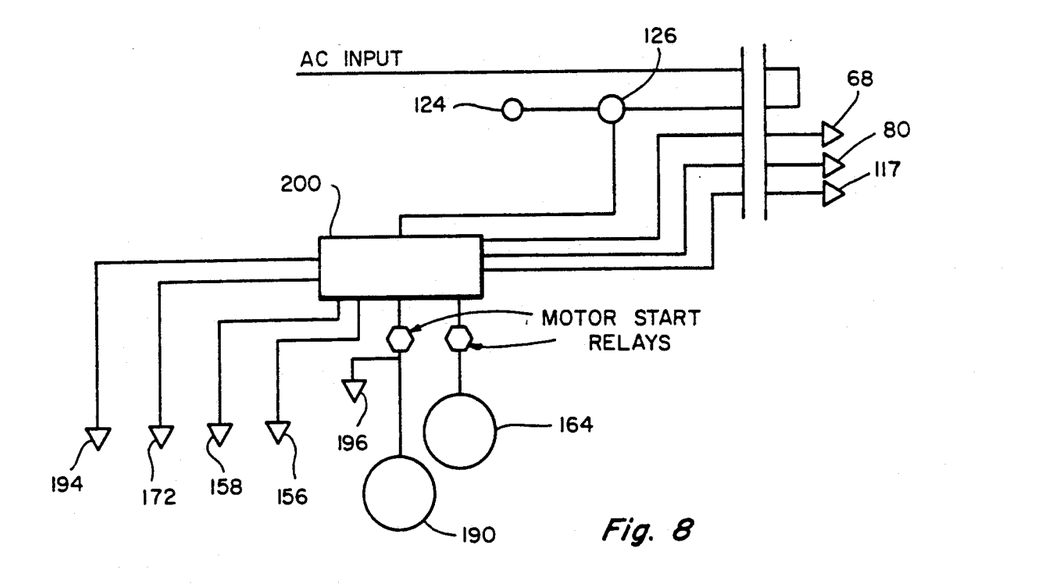
FIG. 8 is a schematic circuit diagram of the circuits for the two units shown in FIG. 7.

FIG. 8 is a simplified circuit diagram showing the electrical connections for the various devices and system included in the units 10 and 120. The electrical system is shown including a relay assembly (or microprocessor) 200 which has connections to the various solenoid valves and relays that have been indentified above. This includes the solenoid valves 68, 80 and 117 located in the unit 10 and which are connected to the electric energy source only when the units 10 and 120 are connected together by the electrical connection lead 136 and 138 recepticle as described. The solenoid valves and other electrical devices in the unit 120 are also in the circuit.

Thus there has been shown and described novel means for safely accumulating waste materials such as body fluids and the like from a patient either by gravity drain or suction, and to the means for rinsing, flushing, decontaminating and resupplying decontaminant to the waste collection means all of which fulfill all of the objects and advantages sought therefor. It will be apparent to those skilled in the art, however, that many changes, modifications, variations and other uses in applications for the subject device are possible, and all such changes, modifications, variations uses and other applications which do not depart from the spirit and scope of the invention are deemed to be covered by the invention which is limited only by the claims which follows.

I claim:

1. A device for decontaminating body fluids from a patient, said device including means for collecting, disinfecting and disposing of body waste materials accumulated from a patient comprising
   container means forming first and second collection chambers each having an upper and a lower end, the upper and a lower ends respectively being at substantially the same elevations,
   first conduit means connecting the lower ends of the collection chambers for communication therebetween,
   second conduit means connecting the upper ends of the collection chambers, said second conduit means having a substantially smaller cross sectional flow capacity than the first conduit means,
   an inlet port to the container means forming the first collection chamber,
   an outlet port connected to the container means forming the second collection chamber, and
   an inlet conduit having a first end connected to the inlet port and an opposite open end for exposing to waste materials to be collected.

2. The device of claim 1 wherein the container means forming the first and second collection chamber include a pair of vertically oriented containers each including a side wall which si closed by upper and lower end walls.

3. The device of claim 1 including a support structure and an enclosure for supporting and housing the container means forming the collection chambers.

4. A medical waste collection system comprising:
   a primary collection and waste treatment unit for decontaminating body fluids including container means forming first and second chambers each having a closed side wall and closed upper and lower end walls, the upper and lower end walls being respectively at substantially the same elevations, first conduit means connected between the upper end walls and second conduit means connected between the lower end walls of the chambers and communicating the pair of chambers thereat, the first conduit means having a substantially smaller cross sectional flow area than the second conduit means,
   an inlet o the first of said chambers at an intermediate location between the upper and lower chamber end walls,
   an open ended drainage conduit having one end connected with the inlet and an opposite open end of exposing to body fluids to be collected, and
   another conduit having one end communicating with a predetermined environment and an opposite end communicating with the second chamber such that the predetermined environment will be present in said first and second chambers.

5. The medical waste collection system of claim 4 wherein the predetermined environment is a suction source.

6. The medical waste collection system of claim 4 wherein the predetermined environment is the ambient atmosphere.

7. The medical waste collection system of claim 4 including a supply of liquid disinfectant filling predetermined portions of the first and second chambers and the second conduit means.

8. The medical waste collection system of claim 4 including an assembly connected to the primary collection and treatment unit for rinsing, flushing and cleaning the primary collection and waste treatment unit including means for supplying a predetermined quantity of disinfectant into the first and second chambers.

9. The medical waste collection system of claim 4 including a flush connection inlet connected to communicate an upper portion of each of said first and second chambers with a source of flushing liquid, and separate normally closed solenoid operated valve means to control the flow of flushing fluid to said first and second chambers.

10. The medical waste collection system of claim 4 including a drain conduit and associated valve means connected to the second conduit means.

11. The medical waste collection system of claim 4 including a housing and support structure for enclosing and supporting the container means, and means attached to the support structure to make the structure mobile.

12. The medical waste collection system of claim 11 including gage means mounted on the housing and support structure, said gage means including a float positioned in one of said first and second chambers for floating on the fluid contained therein, rod means connected to the float and extending upwardly therefrom and means for slideably receiving the rod means including means to indicate the vertical position thereof.

13. The medical waste collection system of claim 8 wherein the rinsing, flushing and cleaning assembly includes conduit means for connection at one end to a source of rinsing and flushing fluid and having a connection at the opposite end to the collection and treatment unit to supply rinsing and flushing fluid to the first and second chambers.

14. The medical waste collection system of claim 8 wherein the rinsing, flushing and cleaning assembly includes a source of fluid disinfectant, and conduit means for supplying disinfectant fluid from said source to the first and second chambers, said last named means including means to control the depth of the liquid disinfectant supplied to the first and second chambers.

15. The medical waste collection system of claim 8 including first solenoid valve means for controlling the supply of rinsing and flushing fluid from said rinsing, flushing and cleaning assembly to the first and second chambers, and second solenoid valve means for controlling the flow of fluid from the first and second chambers to and from the second conduit means.

16. The medical waste collection system of claim 15 including electrical connection means in said rinsing, flushing and cleaning assembly to enable energizing the solenoid valves.

17. The medical waste collection system of claim 16 including means for establishing an electrical connection between the primary collection and treatment unit and the rinsing, flushing and cleaning assembly.

18. The medical waste collection system of claim 4 including second container means forming other adjacent first and second chambers each having a side wall and closed upper and lower end walls and respective first and second conduit means communicating the upper ends and the lower ends of the chambers, one of said chambers of said other adjacent first and second chambers having an inlet at an intermediate location between the upper and lower chamber ends and an open ended drainage conduit having one end connected to the inlet and an opposite end for exposing to body fluids to be collected.

19. The medical waste collection system of claim 12 including a pressure release valve means associated with the means slideably receiving the rod means, said pressure release valve means being engageable by the rod means in a predetermined position thereof to release pressure in the first and second chambers and terminate suction collection of body waste materials.

20. A device for decontaminating body fluids as they are collected form a patient comprising
   a pair of adjacent containers each having closed upper and lower end arranged to be respectively at substantially the same elevations,
   an inlet to one of said containers connected to one end of an inlet conduit, the opposite end of which is positioned to have body fluids enter thereat,
   an outlet to the other of said containers for connection to an environment of predetermined pressure,
   drain conduit means communicating the lower ends of the pair of adjacent containers,
   means for supporting the pair of containers in upstanding position, and
   pressure equalizing conduit means communicating the upper ends of the pair of adjacent containers, said pressure equalizing conduit means having a more restricted flow capacity than the drain conduit means.

21. A device for decontaminating body fluids as they are collected from a patient comprising
   a pair of adjacent containers each having closed upper and lower ends arranged to be respectively at substantially the same elevations,
   a conduit connecting the upper ends of the containers,
   an inlet to one of said containers connected to one end of an inlet conduit, the opposite end of which is positioned to have body fluids enter thereat,
   an outlet to the other of said containers for connection to an environment of predetermined pressure,
   drain conduit means communicating the lower ends of the pair of adjacent containers,
   means for supporting the pair of containers in upstanding position, and
   cleaning and rinsing conduits connected to the upper ends of the pair of adjacent containers for connecting the containers to a source of cleaning and rinsing fluid, and valve means for controlling communication through the cleaning and rinsing conduits between the source of cleaning and rinsing fluid and the insides of the pair of adjacent containers.

22. A device for decontaminating body fluids as they are collected from a patient comprising
   a pair of adjacent containers each having closed upper and lower ends arranged to be respectively at substantially the same elevations,
   an inlet to one of said containers connected to one end of an inlet conduit, the opposite end of which is positioned to have body fluids enter thereat,
   an outlet to the other of said containers for connection to an environment of predetermined pressure,
   a conduit connecting the upper ends of the containers, drain conduit means communicating the lower ends of the pair of adjacent containers,
   means for supporting the pair of containers in upstanding position, and
   a housing for containing and supporting the pair of containers, said housing having an outlet fitting for connection to the outlet drain conduit means.

23. A device of claim 22 including means for supporting the housing on wheels.

24. A device for decontaminating body fluids as they are collected from a patient comprising
   a pair of adjacent containers each having closed upper and lower ends arranged to be respectively at substantially the same elevations,
   a conduit connecting the upper ends of the containers,
   an inlet to one of said containers connected to one end of an inlet conduit, the opposite end of which is positioned to have body fluids enter thereat,
   an outlet to the other of said containers for connection to an environment of predetermined pressure,
   drain conduit means communicating the lower ends of the pair of adjacent containers,
   means for supporting the pair of containers in upstanding position, and
   check valve means associated with the inlet to said one container to permit flow into but not out of said one container.

25. A device for decontaminating body fluids as they are collected from a patient comprising
   a pair of adjacent containers each having closed upper and lower ends arranged to be respectively at substantially the same elevations,
   a conduit connecting the upper ends of the containers,
   an inlet to one of said containers connected to one end of an inlet conduit, the opposite end of which is positioned to have body fluids enter thereat,
   an outlet to the other of said containers for connection to an environment of predetermined pressure,
   drain conduit means communicating the lower ends of the pair of adjacent containers,
   means for supporting the pair of containers in upstanding position, and
   a vacuum source and means connecting the vacuum source to the outlet.

26. A device for decontaminating body fluids as they are collected from a patient comprising
   a pair of adjacent containers each having closed upper and lower ends arranged to be respectively at substantially the same elevations,
   a conduit connecting the upper ends of the containers,
   an inlet to one of said containers connected to one end of an inlet conduit, the opposite end of which is positioned to have body fluids enter thereat,
   an outlet to the other of said containers for connection to an environment of predetermined pressure,
   drain conduit means communicating the lower ends of the pair of adjacent containers,
   means for supporting the pair of containers in upstanding position, and
   means connecting the outlet to atmospheric pressure.

* * * * *

UNITED STATES PATENT AND TRADEMARK OFFICE
CERTIFICATE OF CORRECTION

PATENT NO. : 5,242,434

DATED : September 7, 1993

INVENTOR(S) : William M. Terry

It is certified that error appears in the above—identified patent and that said Letters Patent is hereby corrected as shown below:

Column 7, line 30, "o" should be --on--.

Column 8, line 7, "5" should be --52--.

Column 10, line 20, "t" should be --to--.

Column 11, line 37, "si" should be --is--.

Column 11, line 55, "o" should be --to--.

Column 13, line 18, "form" should be --from--.

Signed and Sealed this

Fifteenth Day of March, 1994

Attest:

BRUCE LEHMAN

Attesting Officer

Commissioner of Patents and Trademarks